United States Patent [19]

Bennewitz

[11] Patent Number: 4,495,953
[45] Date of Patent: Jan. 29, 1985

[54] APPARATUS AND METHOD FOR PRODUCING AND USING DIRECTIONAL, ELECTRICAL AND MAGNETIC FIELDS

[76] Inventor: Paul F. Bennewitz, 1413 Wagontrain, SE., Albuquerque, N. Mex. 87123

[21] Appl. No.: 331,020

[22] Filed: Dec. 15, 1981

[51] Int. Cl.³ .............................................. A61N 1/36
[52] U.S. Cl. .................................. 128/789; 128/419 R
[58] Field of Search ............... 128/653, 419 R, 419 N, 128/419 E, 419 F, 419 D, 419 C, 789, 804; 324/58 R, 58 A, 58 B; 179/107 E, 107 FD

[56] References Cited

U.S. PATENT DOCUMENTS 4,135,131  1/1979  Larsen et al. .................... 128/653 X
4,344,440  8/1982  Aaby et al. ......................... 128/653

Primary Examiner—Kyle L. Howell
Assistant Examiner—Francis J. Jaworski
Attorney, Agent, or Firm—Cahill, Sutton & Thomás

[57] ABSTRACT

An electrical transducer includes a magnet having first and second poles, a paramagnetic flux concentrator, and a diamagnetic spacer disposed between the flux concentrator and one pole of the magnet. The transducer produces a directional magnetic field region and a directional, approximately linearly decreasing, electric field along an axis of the flux concentrator and substantially beyond the magnetic field. The transducer produces variations in portions of the directional electric field extending beyond the magnetic field region in response to variations caused in the magnetic field by excitation of a coil surrounding the flux concentrator. Variations in the electric field intensity in the region of the directional electric field cause corresponding variations in the magnetic field produced by a sensor. Those variations are sensed using a Hall effect sensor. A method of two-way communication between a nerve into which the directional field extends is disclosed. One of the disclosed devices is used as an improved hearing aid that aims the directional electrical field into nerves in a person's inner ear to produce electrical signals representing sound in those nerves.

25 Claims, 14 Drawing Figures

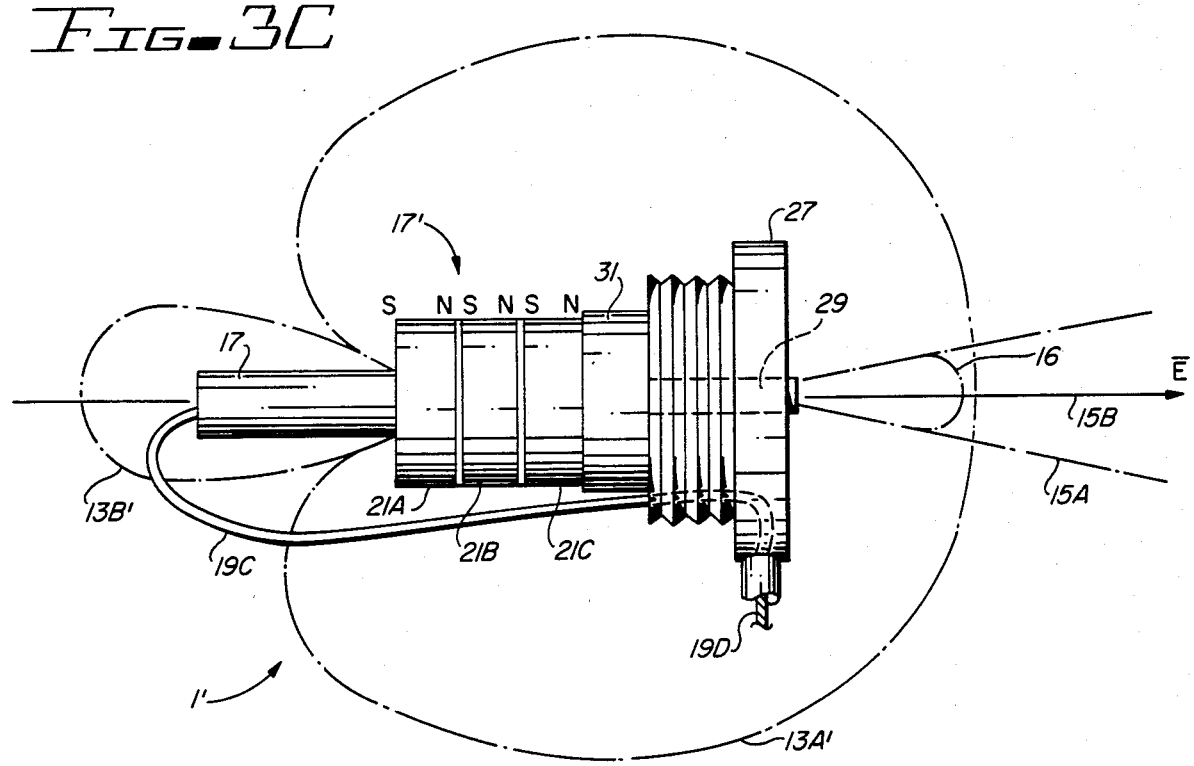
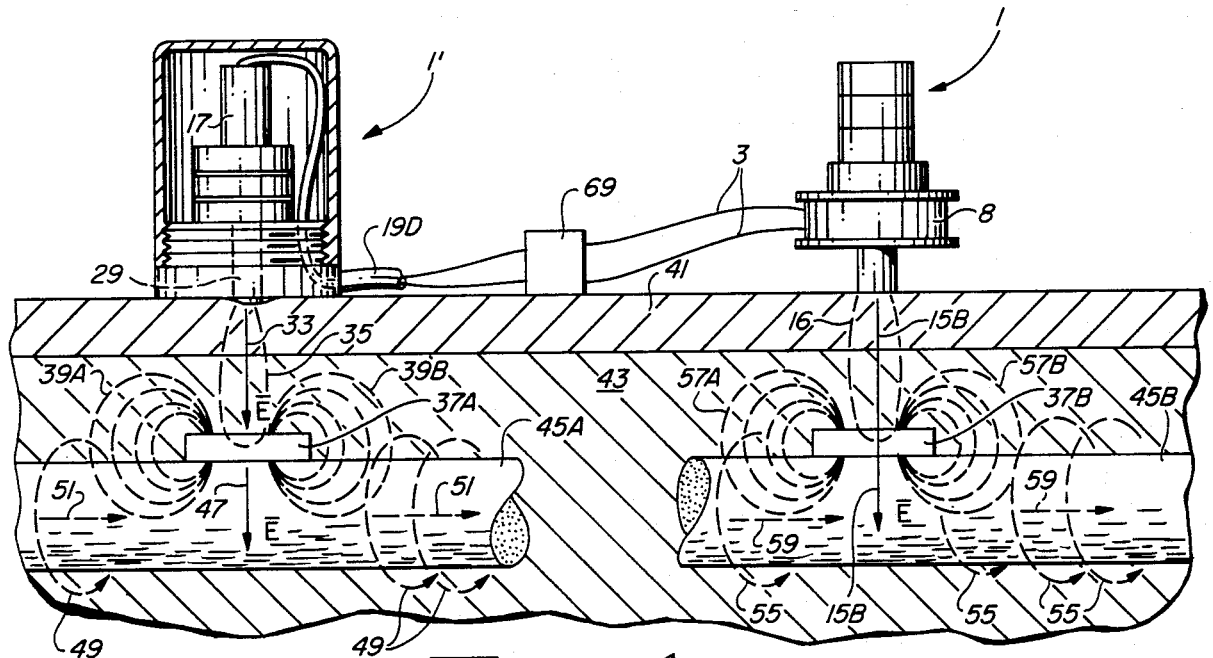

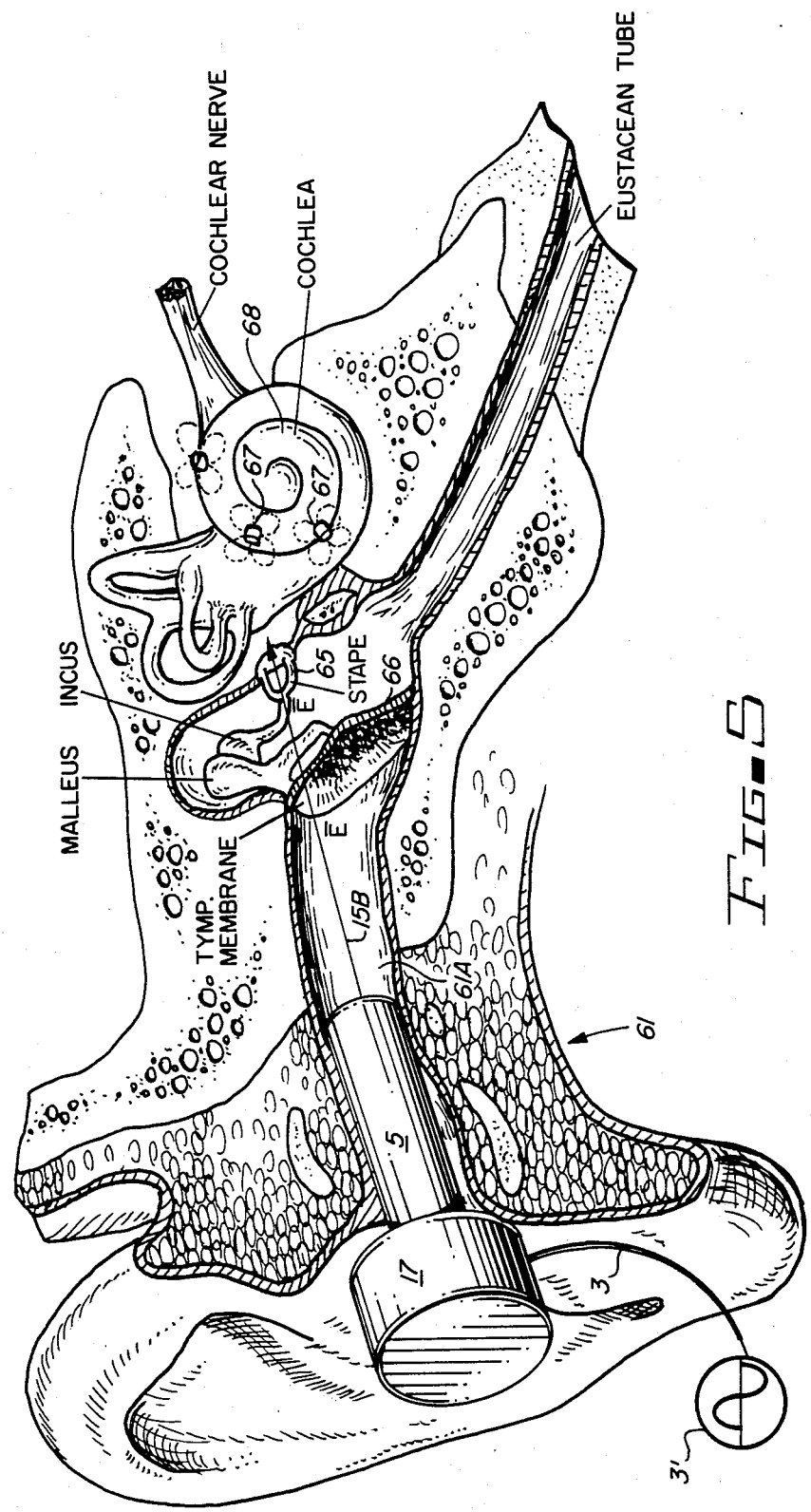

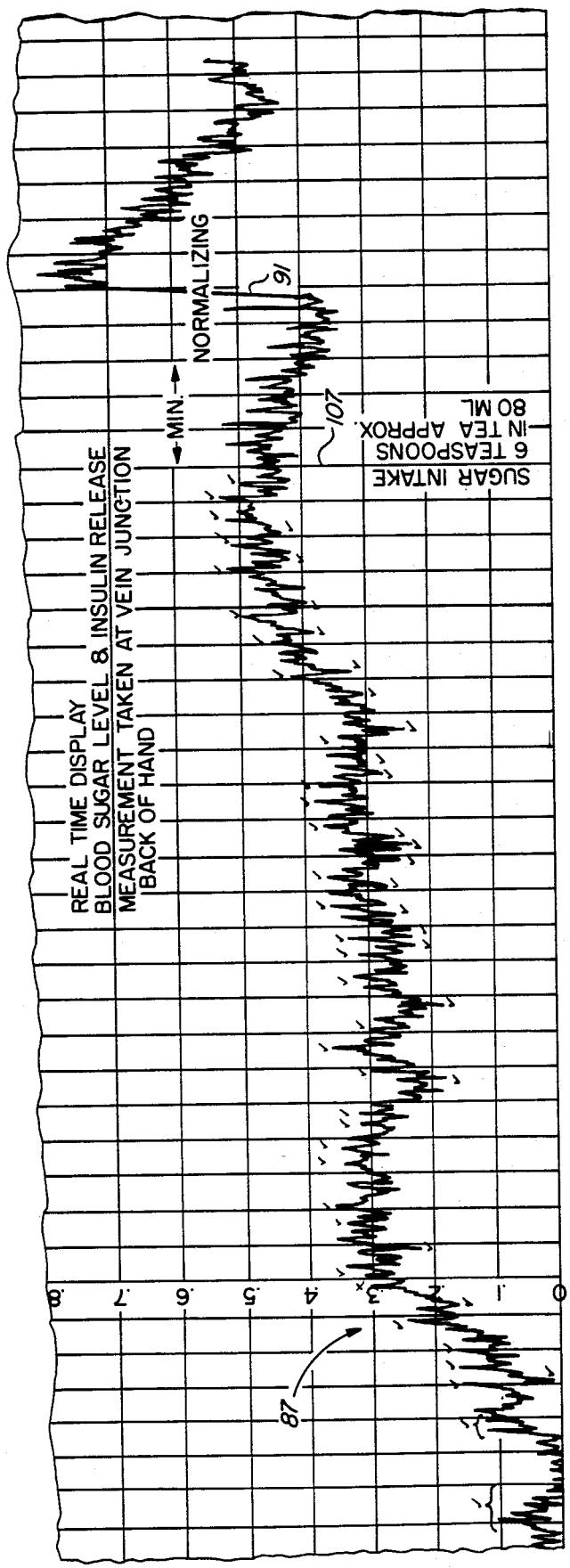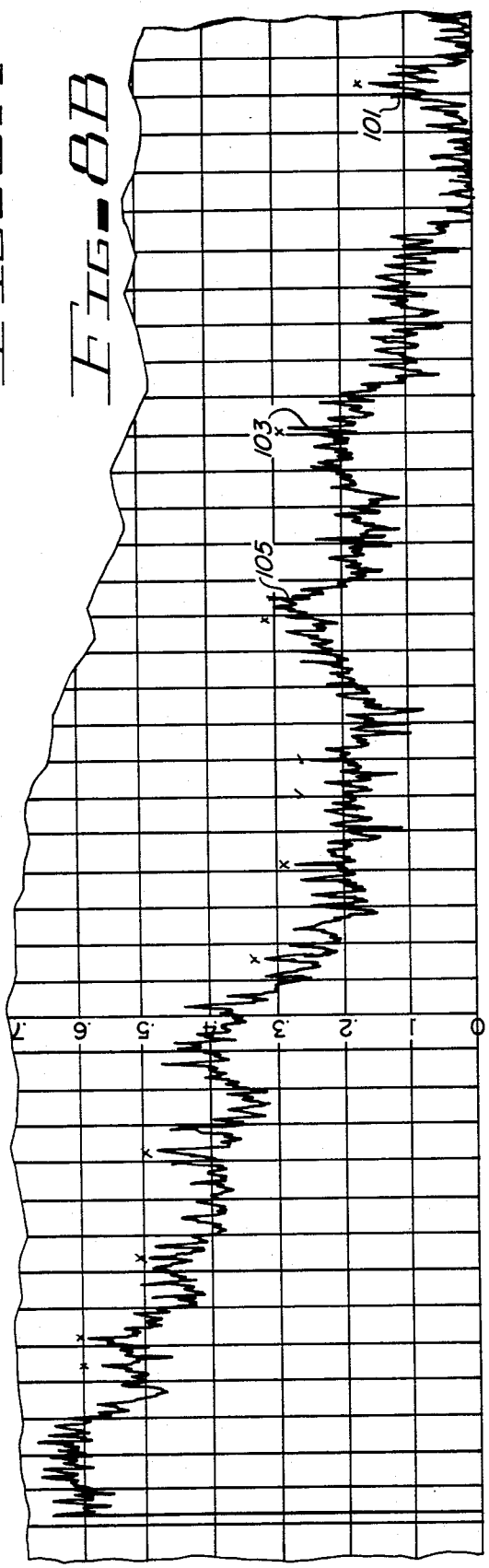

APPARATUS AND METHOD FOR PRODUCING AND USING DIRECTIONAL, ELECTRICAL AND MAGNETIC FIELDS

BACKGROUND OF THE INVENTION

The invention relates to devices and method for producing focused electric fields, and also to using such devices and methods to sense naturally occurring electric signals in human nerve cells and to produce controlled electrical signals in human nerve cells.

Various techniques have been used to sense signals produced in human nerve cells. For example, "invasive" procedures involving insertion of electrical probes into nerve cells to measure signals therein have been practiced. Such procedures are obviously undesirable, as they risk injury to the person (or animal) involved. Devices using skin contact electrodes have been utilized to sense the level of electrical activity in the brain. However, precise measurement of electrical activity in a single nerve cell cannot be accomplished using this method. Invasive probes and electrodes that contact the skin of a person have been used to produce electrical signals in nerves, but are subject to the same shortcomings as use of the above techniques for sensing nerve signals. There would undoubtedly be numerous beneficial uses for any devices and techniques that would have the capability of accurately sensing electrical signals in individual nerve cells and introducing accurately controlled signals from external sources into nerve cells without the necessity for invasive techniques that penetrate the surface of the nerve cell.

Therefore, it is an object of the invention to provide a device and method for accurately sensing a normally occurring electrical signal in a nerve of a human or animal without necessitating any invasion of the nerve by any apparatus.

It is another object of the invention to provide a device and method for accurately producing a controlled electric signal in a nerve of a human or animal without necessitating invasion of the nerve by any apparatus or surgical procedure.

It is another object of the invention to provide a device and method for measuring electrical signals in a human or animal brain.

Conventional hearing aids operate by amplifying the intensity of sound in a patient's ear to very high levels that can be heard by persons with damaged hearing systems. However, the fidelity and accuracy of the sounds actually heard by the hearing impaired or deaf person are often quite poor, depending on the nature of the person's hearing impairment. Despite improvements that have been made in hearing technology, there remains a need for a method and apparatus for improving the quality of sounds heard under various conditions by hearing and hearing impaired persons alike.

Therefore, it is another object of the invention to provide an improved hearing aid apparatus and method.

It is another object of the invention to provide an improved method and apparatus for producing and utilizing focused electric fields.

SUMMARY OF THE INVENTION

Briefly described, and in accordance with one embodiment thereof, the invention provides a device and method for producing a focused, highly directional electric field region and an extending, focused magnetic field region along a common axis, the directional electric field region extending substantially beyond the magnetic field region. In a described embodiment of the invention, one or more magnetic discs are positioned adjacent to each other with opposite poles adjoining, one end of the magnetic disc or stack of magnetic discs being positioned in a predetermined spaced relationship to a paramagnetic element for concentrating magnetic flux produced by the magnets. Diamagnetic material is disposed between one end of the flux concentrator and the nearest magnetic disc. It has been found that a focused region in which a directional electric field is present in a measurable amount extends along an axis of the flux concentrator for a distance substantially beyond the region of measurable magnetic field strength. The magnetic field strength decreases approximately inversely proportionally to approximately the third power of the distance from one end of the flux concentrating element along the axis thereof. The electrical field strength along the axis of the flux concentrating element decreases approximately linearly with distance along the axis of the flux concentrator. The strengths of the magnetic and electrical fields in the respective focused regions increase as the strengths of the magnetic discs are increased. The strengths of the magnetic and electrical fields also increase up to a maximum and then decrease as the distance between the flux concentrating element and the closest magnetic disc is increased along the axis of the flux concentrator. In some of the described embodiments of the invention, a diamagnetic foam rubber disc of preselected thickness separates one end of the flux concentrator from the nearest magnetic disc. The flux concentrating element includes an elongated section of soft iron rod. In one embodiment of the invention, a coil with windings through which the flux concentrator passes has input terminals to which an electrical input signal is applied. Corresponding variations in both the directional magnetic field region and the electrical field region are produced in response to the input signal, thereby providing a transmitting device that can produce controlled variations in electric field strength in the region in which the above described electric field extends. When other variations in the electric field occur (as a result of external influences) in the region into which the directional electrical field extends, corresponding variations in the magnetic field are produced by the described device and are sensed by the coil. In one embodiment of the invention, a Hall effect sensor is positioned to sense these variations of magnetic field at an opposite end of the magnetic disc, thereby providing a sensing device that can sense variations in electrical field strength in a region into which the above mentioned directional electric field extends. In applications of the invention, the described transmitting and sensing devices are respectively utilized to inject or produce controlled electrical signals in nerve cells and to sense neural electric signals occurring in nerve cells. In one embodiment of the invention, wherein the north poles of the magnetic discs are oriented outward and the axis of the flux concentrator is oriented toward hearing centers in a human ear, without physically penetrating the skin of the subject, electrical signals representing audio sounds are induced in nerve cells in the hearing centers of the inner ear structure, causing persons with impaired hearing to accurately "hear" the sounds represented by the signals applied as inputs to the coil. In one described embodiment of the invention, two of the devices of the present invention can be utilized to bridge the gap between sections of a severed nerve without invasion of any portion of the devices into the sections of the severed nerve.

In another embodiment of the invention, the above-mentioned sensing device is used to non-invasively detect electrical activity in blood circulating through a subject's vein, wherein the electrical activity indicates the level of sugar in the blood. In another embodiment of the invention, the above mentioned sensing device is used to non-invasively monitor neural signals associated with various physiological processes, such as breathing. In another embodiment of the invention, the above described sensing device is used to monitor neural signals produced in a subject's brain.

BRIEF DESCRIPTION OF THE DRAWINGS

FIG. 3C is a schematic diagram illustrating the device of FIG. 3B and showing the extent of the magnetic and electric fields generated by the device of FIG. 3B.

FIG. 4 is a schematic diagram illustrating use of the devices of FIGS. 1 and 3B to accomplish bridging of a gap between portions of a severed nerve.

FIG. 5 is a schematic diagram useful in explaining utilization of the device in FIG. 1 as a hearing enhancement device.

FIGS. 8A and 8B together constitute a substantial copy of a real time plot traced by an electronic plotter of the output of the device of FIG. 3D placed against a vein on the back of the hand of the inventor to measure electrical currents in the blood representing his blood sugar level after ingesting a predetermined quantity of sugar.

DESCRIPTION OF THE INVENTION

Figure 1:
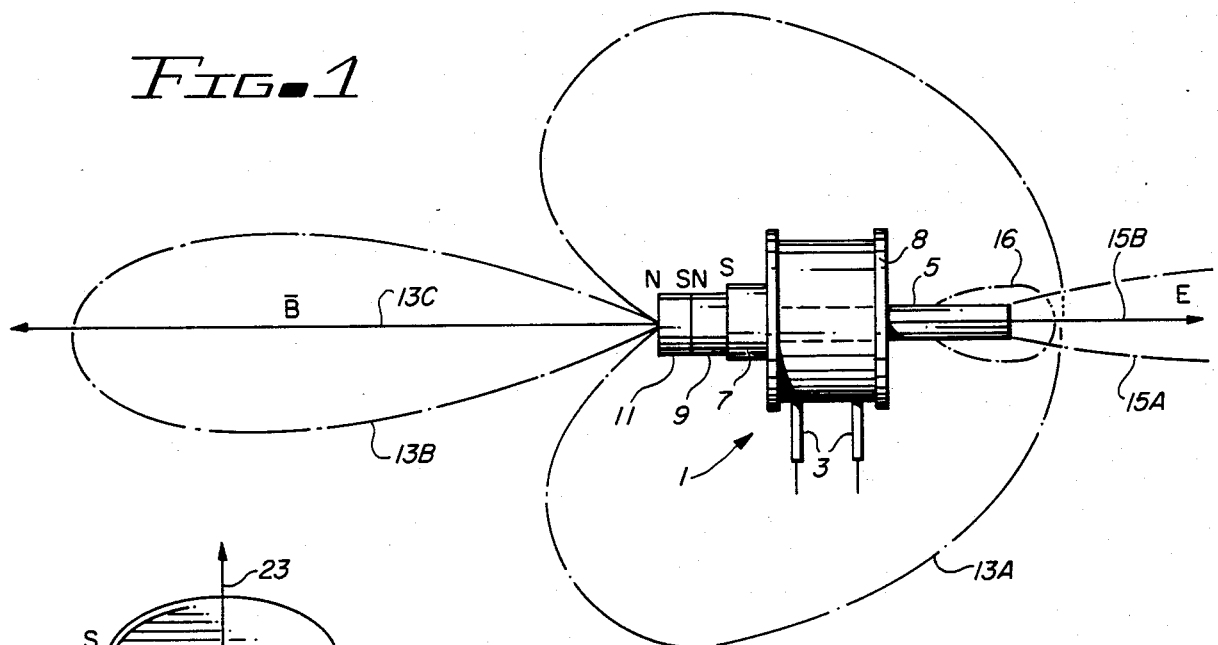
FIG. 1 is a schematic view of one embodiment of the present invention, indicating the extent of focused magnetic and electric field regions produced by the device.

Referring now to FIG. 1, device 1, hereinafter referred to as transducer 1, includes one or more disc-shaped permanent magnets such as 9 and 11, a diamagnetic spacer 7, a paramagnetic flux concentrator element 5, and a coil 8 having two leads 3. Permanent magnets 9 and 11 can be disc-shaped devices having a diameter of 0.250 inches and a thickness of 0.100 inches, and are commercially available devices having a catalog part number 90C90A, manufactured by Hicorex. The north pole of each of magnets 9 and 11 is oriented to the left of FIG. 1, so that the north pole of magnetic disc 9 and the south pole of magnetic disc 11 are adjoining.

Diamagnetic spacer 7 can be any suitable diamagnetic material, and can, for example, be implemented by means of a foam rubber disc having a thickness of approximately one-fourth of an inch. The left face of foam disc 7, as shown in FIG. 1, adjoins the south pole of magnetic disc 9, and the right face of foam disc 7 adjoins the left face of coil 8.

Flux concentrator element 5 can be composed of soft iron rod material having a diameter of approximately one-eighth of an inch and a length of approximately one-half of an inch. The left end of flux concentrator 5 adjoins or abuts the right face of foam disc 7.

Coil 8 can be implemented by means of a 50 gauge coil having 1,495 bifilar turns, commercially available as part number C101A from Thunder Scientific Corporation of Albuquerque, N.M. As subsequently explained, coil 8 is omitted from certain embodiments of the invention, such as the embodiment of FIG. 3C.

The purpose of coil 8 is either to sense variations in the magnetic field produced by transducer 1 in response to externally produced variations in the electric field in focused E field region 15A, or to induce variations in the electric field region 15A of transducer 1 in response to electrical input signals applied between conductors 3 of coil 8.

It has been discovered that the transducer of FIG. 1, with or without coil 8 actuated, produces a magnetic field having the extent or boundary designated by dotted line 13A. The magnetic field having the boundary 13A is hereinafter referred to as the "magnetic sphere".

Transducer 1 also produces a magnetic field having the extent or boundary indicated by dotted line 13B. This portion of the magnetic field produced by transducer 1 is referred to hereinafter as the "rear lobe". Reference numeral 13C designates a vector aligned with a center axis of transucer 1 to indicate the direction and intensity of the magnetic "B" field along the axis of and in the direction of vector 13C.

It has been discovered that the transducer 1 also produces a directional electric field in region 15A shown by dotted lines and a directional magnetic region 16 that both extend outwardly and generally axially from the right end of flux concentrator 5. Dotted lines 15A designate the general boundaries of the above-mentioned electrical field and reference numeral 15B designates a vector that represents the electric field intensity and the direction of the electric field along the longitudinal axis of transducer 1.

It has been found that the magnetic field strength in directional magnetic field region 16 decreases approximately inversely to the third power of distance to the right from the end of flux concentrator 5 along the axis thereof.

It also has been found that the intensity of the electric field represented by vector 15B in FIG. 1 decreases in an approximately linear fashion with distance along the longitudinal axis of transducer 1. It has further been found that the intensity of the electric field in the region bounded by dotted lines 15A decreases roughly exponentially with distance away from and perpendicular to the axis of flux concentrator 5.

The device used for measuring the field strength surrounding the device of FIG. 1 includes a Hall effect sensor (implemented by means of a type TL173C Linear Hall effect sensor manufactured by Texas Instruments) having its output connected to the inputs of a differential amplifier (which can be implemented by means of a MA776 integrated circuit single ended amplifier manufactured by Fairchild, Inc). The output of the amplifier is connected to a meter (implemented by means of a conventional sensitive digital volt meter manufactured by John Fluke, Inc). The Hall effect sensor was placed within a few millimeters of the right end of flux concentrator 5 and was moved away from transducer 1 in spaced increments of 1 millimeter. The transducer 1 was rotated 360° on a rotatable platform, while the Hall effect sensor was stationary to obtain field strength measurements at each incremented distance away from transducer 1. The readings of the meter were taken for each incremented position until significant meter readings were no longer obtained. This procedure was followed to obtain the meter readings in the entire region surrounding the transducer 1. Note that the boundaries shown in FIGS. 1 and 2 have been modified slightly to correct for a skew of rear lobe 13B of approximately 15 degrees. (Later investigation proved this skew to be caused by slight misalignment of the magnets 9 and 11 to the center line of the concentrator 5.) The E vector 15B extends beyond approximately 200 centimeters from transducer 1. The directional magnetic region 16 extends to as much as approximately 1.5 centimeters from the end of flux concentrator 5. The magnetic sphere 13A extends to approximately as much as 1.5 centimeters to the right of the end of flux concentrator 5 and approximately equally above and below the horizontal axis thereof, as shown in FIG. 1. Rear lobe 13B extends to approximately 1.75 centimeters to the left of magnetic disc 11.

Figure 2:
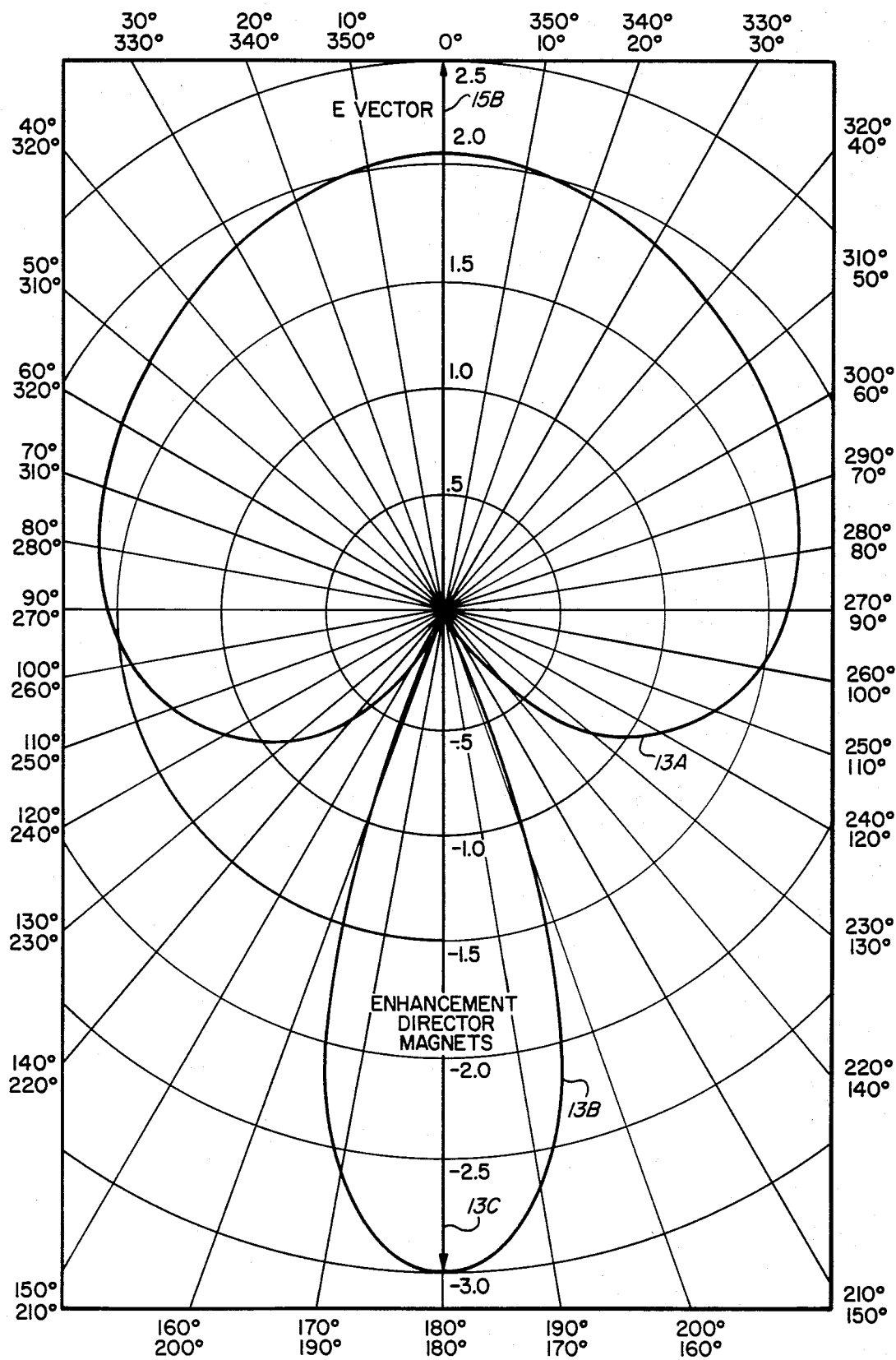
FIG. 2 is a polar plot of data representing the magnetic field intensity and electric field intensity of the fields produced by the device of FIG. 1.

Next, experiments were performed to determine whether the fields in the regions indicated by the dotted line in FIG. 1 and the solid lines 13A and 13B in FIG. 2 and by dotted line 15A in FIG. 1 were magnetic fields or electrical fields. One of the experiments performed was to place a coil having four windings between the input terminals of an oscilloscope (a Model Number 3400 Storage oscilloscope manufactured by Gould, having a scale setting of 20 MV volts per division). The coil was then manually moved rapidly in the regions surrounding transducer 1. Such movement within the regions indicated by reference numerals 13A, 13B and 16 in FIGS. 1 and 2 produced significant deflection of the trace on the oscilloscope, indicating that the fields in these regions are magnetic fields. Rapid movement of the coil in the conical region bounded by reference numeral 15A beyond magnetic sphere 13A and region 16 produced no deflection of the oscilloscope trace, indicating that the field in conical region 15A is an electric field.

Several additional experiments were carried out to further prove the existence of the electric field beam or voltage vector 15B using ion guns to shoot charged ions toward the portion of the beam 15B extending beyond the magnetic sphere 13A. It was believed that if the electric field beam 15B does actually exist beyond the magnetic sphere 13A, the electrical field beam 15B should "take up" such charge.

The initial experiment utilized a simple, inexpensive, commercially available ion gun of the type intended to be used for removing electrical charge from phonograph records. This type of ion gun includes a strip of piezoelectric material (barium titanate, in this case) which is stressed by bending it in one mode or the other. Such stressing releases a stream of ions, the polarity of which depends upon the direction in which the material is bent. The gun has a trigger which, when pushed in one direction, stresses the barium titanate in one mode, producing a stream of positive ions. If the trigger is pushed in the opposite direction, the barium titanate is stressed in the opposite mode, producing a stream of negative ions.

The device of FIG. 1 was placed on one end of a cable and aimed at a Hall effect transducer positioned roughly two-thirds of a meter away on the table. More specifically, the longitudinal axis of the free end of the flux concentrator 5 was aimed at the Hall effect transducer, and the Hall effect transducer was located on the table to the right of the device of FIG. 1.

The inputs of a storage oscilloscope were connected to the leads 3 of coil 8 of the device of FIG. 1. The output of the Hall effect transducer was amplified by an amplifier, and the resulting amplified signal was measured by an ordinary meter. The above mentioned ion gun was positioned at various points along a line spaced from and parallel to the axis of the flux concentrator 5, so that when the ion gun was fired, a burst of ions would travel perpendicularly toward the electric field beam 15B.

The result was that when the ion gun was fired at any point along the line forming the axis of the flux concentrators within approximately 4 meters to either the right or left of the device of FIG. 1, the meter would deviate from an equilibrium level to the positive or negative limit of the amplifier, depending upon whether the ions fired were positive or negative, respectively. It was also found that the amount of deviation of the meter was essentially a linear function, i.e., that the magnitude of the deviation of the meter decreased essentially proportionally with distance along the axis of flux concentrator 5 to the right away from the device of FIG. 1.

The meter measurement also indicated that the electric field beam 15B "held" the charged ions briefly, and that then the charge slowly leaked off into the atmosphere. Depending upon the humidity of the air, the meter reading took as long as five to ten minutes to return to its equilibrium level.

Subsequently, a "continuous wave" ion gun was constructed utilizing a pointed electrode with a 16,000 volt D.C. potential applied thereto and with an oxygen-nitrogen gas mixture flowing past it. This caused ionization of the gas mixture, producing a continuous stream of charged ions. With the gain of the above-mentioned amplifier suitably adjusted, it was found that the electric field beam 15B was repetitively charged to a maximum level, and that each time the maximum level was attained, a partial discharge occurred. The trace on the storage oscilloscope indicated the repetitive charging and partial discharging of the beam.

The results of the above-mentioned ion beam experiments show first, that the electron field beam or voltage vector 15B does indeed exist beyond the magnetic field 13A, and that the field strength of the electric field beam 15B decreases essentially linearly along the axis of the flux concentrator, and finally, that externally produced changes in the potential of the region through which the beam 15B penetrates result in corresponding changes in the magnetic field of the device of FIG. 1 (thereby inducing a measurable voltage on leads 3 of the coil 8, or, alternatively, producing a variation in the output of a Hall effect device that is positioned in the changing magnetic field).

Figure 3A:
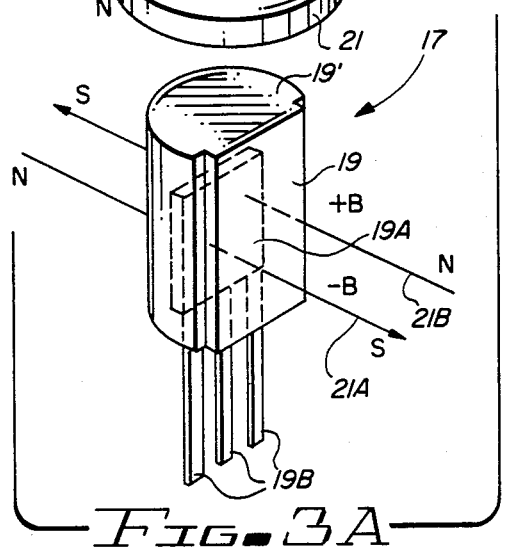
FIG. 3A is a perspective diagram showing use of a Hall effect device to sense variations in the magnetic field produced by the device of FIG. 1.

FIG. 3A shows a Hall effect magnetic field sensing device. It includes Hall effect sensor 17 which can be implemented by means of a Texas Instruments TL-173 integrated circuit Hall effect device. Reference numeral 19A designates an integrated circuit Hall effect chip housed within the structure indicated by reference numeral 19. Three leads 19B extend from one end of housing 19. Reference numerals 21A and 21B designate the convention used to define positive and negative directions for the B field being sensed. Reference numeral 21 designates a magnetic disc having its north and south poles as indicated in FIG. 3A axially aligned, as indicated by arrow 23, with Hall effect sensor 17 to function as a flux concentrator.

Figure 3D:
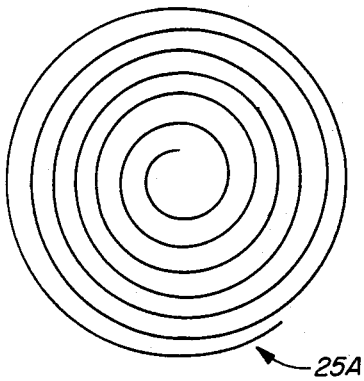
FIG. 3D is a plan view of a indium wire coil utilized between the permanent magnets of the device shown in FIG. 3B to compensate for temperature variations in the operation of that device.
Figure 3B:
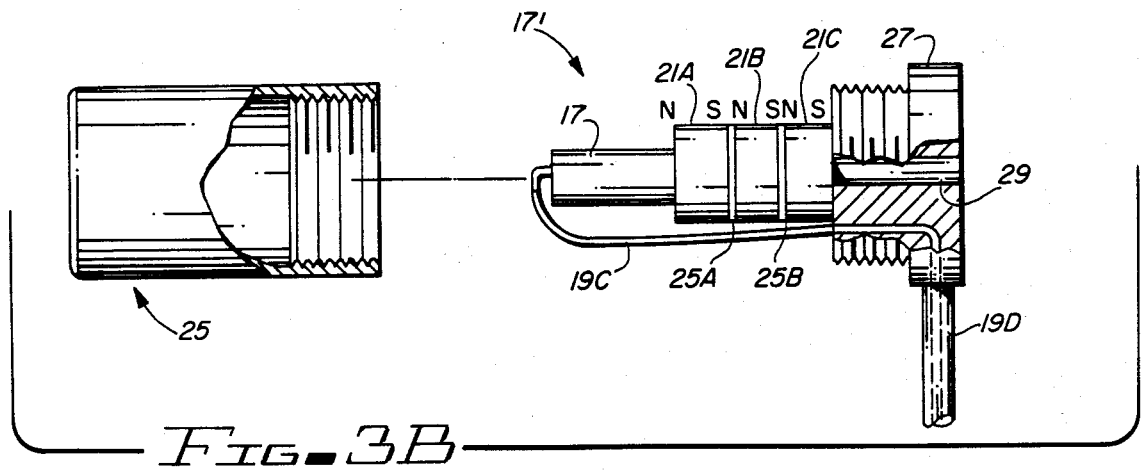
FIG. 3B is a partially exploded, partially cutaway view of another embodiment of the invention useful as a sensor and incorporating a Hall effect sensor device of the type shown in FIG. 3A.

FIG. 3B discloses a practical Hall effect sensing device 17' constructed along the lines of the device shown in FIG. 3A. Hall effect sensing device 17' includes a threaded Teflon or nylon base 27 having a hole therein through which a soft iron core magnetic flux concentrator 29 having a diameter of approximately one-eighth of an inch extends. The left end of flux concentrator 29 abuts one face of magnetic disc 21C. Magnetic disc 21B is adjacent to, but separated from magnetic disc 21C by means of indium spacer 25B, which is identical to helical indium wire spacer 25A shown in FIG. 3D. The indium wire can be approximately 25 mils in diameter. Its presence has been found to provide compensation for temperature variation in the magnetic field. Magnetic disc 21A is disposed adjacent to but separated from magnetic disc 21B by means of indium spacer 25A. Hall effect transducer 17 is disposed with its end 19' (FIG. 3A) abutting the left end of magnetic disc 21A, as shown in FIG. 3B. Appropriate wire conductors 18C, respectively connected to appropriate ones of conductors 19B (FIG. 3A), extend along the sides of magnetic discs 21A, 21B, and 21C, through a suitable channel in base 27, and outward through insulative conduit 19D. The threads of cap 25 can be screwed onto the threads of base 27 to provide a sealed unit.

Note that magnetic discs 21A, 21B and 21C are stacked so that their opposed poles are respectively adjacent, so that in combination, they perform the function of concentraing the electric flux whose intensity is being sensed, thereby increasing the sensitivity of Hall effect device 17.

The Hall effect transducer of FIG. 3B can be converted into a transducer 1' that is similar to the transducer 1 shown in FIG. 1 by inserting a diamagnetic spacer 31 between the stack of magnetic discs, in the manner shown in FIG. 3C. For reasons not fully understood, positioning of the diamagnetic spacer 31 between flux concentrator 29 and the adjacent face of magnetic disc 21C causes the structure shown in FIG. 3B to produce the directional, extended E field represented by the E vector 15B in the conical region 15A in FIG. 3C. (Note that the same reference numerals have been utilized to denote the various field regions in both FIGS. 3C and 3A). Note that the directions of magnetic discs 21A, 21B and 21C have been reversed from those shown in FIG. 1. It has been found that this does not significantly modify the boundaries of the field regions, but does have an important effect on sensitivity of the transducer 1' in the manner shown in FIG. 4, subsequently explained.

At this point, it will be helpful to again mention that the transducer 1 shown in FIG. 1 can be used to produce variations in the intensity of the directional E field 15B within the region 15A. By applying a predetermined signal to the leads 3 of coil 8, the additional magnetic flux density thus produced also passes through flux concentrator 5 and is added to the flux density produced by magnetic discs 9 and 11. My experiments have shown that the strength of the electric field intensity in the region 15A varies directly with the amount of current forced through coil 8 via leads 3. (It should be noted that only the portion of region 15A closer to transducer 1 is conical in shape, and that the boundary lines 15A eventually begin to taper back toward the axis of vector 15B as distance from transducer 1 increases.)

Since the directional electric field represented by vector 15B decreases quite slowly (i.e., linearly, rather than proportionally to the inverse third power of the distance from the source of the flux as is the case for the magnetic field strength), it occurred to me to determine if the directional E field 15B could be used to penetrate human nerve cells and thereby create or induce desired signals into human nerves to improve the hearing of deaf or hard of hearing persons.

At this point, it will be helpful in understanding of the invention to describe the series of events that led to discovery of the invention. I was experimenting with Hall effect devices such as those of FIGS. 3A and 3B (without the indium rings 25A and 25B of FIG. 3B) in the course of designing a meter for measuring magnetic field strengths. I was experimenting with disc-shaped magnets, such as 21 (FIG. 3A), 21A, 21B and 21C (FIG. 3B) to concentrate the magnetic flux of the magnetic field to be measured. I discovered that an increase in sensitivity of the device occurred when the distance between a flux concentrator (such as flux concentrator 5 in FIG. 1) and a magnetic disc was increased. I conducted experiments by applying music signals from a tape recorder to the leads 3 of a coil such as coil 8 of FIG. 1. I held the coil close to my head, and was able to "hear" the music signal being applied to the coil. I have found that placing only a flux concentrator, such as flux concentrator 5, with a coil, such as coil 8, thereon driven by a music signal from a tape recorder next to my ear results in no "hearing" of the music, regardless of where the axis of the flux concentrator 5 is oriented or how close it is placed to a human head or how high level of an audio input is applied to the leads of coil 8. However, I have found that if I hold the music driven coil and flux concentrator close to my head and then bring a reasonably powerful magnet to within approximately three inches of the coil and flux concentrator, I immediately "hear" music which seems to be produced in the center of my head. The bass sounds contained in the music signal are especially prominent. Thus, I discovered the above mentioned E vector and was able to duplicate the above results by using appropriately smaller magnets properly aligned with flux concentrator 5 and positioning diamagnetic spacers (instead of air) between the magnets and the flux concentrator 5.

Further experimentation with the devices disclosed herein, has led me to the use of the device as explained in conjunction with FIG. 5.

FIG. 5 discloses use of the transducer 1 of FIG. 1 mounted in a plastic encapsulating device similar to that shown in FIG. 3B, with the portion containing the concentrator 5 extending into the ear canal of a human ear. The coil 8, foam rubber spacer 7, and a suitable number of magnetic discs such as 9 and 11 are contained in a housing in FIG. 5. Lead 3 contains the lead wires of coil 8 (FIG. 1) which are connected to a suitable source of audio input signals, such as a microphone, radio, record player or the like. The above-mentioned directional E field 15B is also shown in FIG. 5 extending into the inner ear of the person.

In FIG. 5, reference numeral 61 designates the internal and external ear structure of the person under discussion, and reference numeral 61A designates the inner ear canal. Reference numeral 65 represents the portion of the ear called the stapes, which acts as a hydraulic amplifier in conjunction with the malleus etc. and amplifies sound impinging on the person's eardrum, to carry the sound into the cochlea, which contains the nerve ends and associated hair-like pickup nerves to convert the sound to electrical signals. In accordance with the present invention, electrical signals representing the incoming sounds are produced by penetration of the E vector 15B into these appropriate nerves, bypassing the eardrum and bones in the inner ear. The audio electrical signal 3' inputted to transducer 1 induces electrical signals corresponding to the music played, and the person actually "hears" music or other information represented by the signals externally applied to input conductors 3. Experiments that I have conducted demonstrate that the device shown in FIG. 5 should be able to greatly enhance the hearing ability of a hearing person who is not deaf or is only partially deaf to sounds carried by sound waves entering his ear and impinging upon his eardrum 66. This is an enhanced frequency range and is apparently reinforced by partial pressure variations occurring in the vicinity and within the E vector.

For a person with normal hearing, it has been found that gain and tonal quality of audio signals generated in response to sounds are greatly improved by use of the device shown in FIG. 5.

It is known that small magnets can act as magnetic field relay devices, since magnetic field forces add vectorially. Therefore, it is believed that one or more "magnetic pills" composed of tiny, suitably encapsulated permanent magnetic discs, denoted by reference numeral 67 in FIG. 5, could be implanted in appropriate portions of the inner ear, such as in the cochlea 60. Such surgically implanted magnetic pills 67, coated with ceramic, should enhance the "injection" or inducement of electrical signals representing the input audio sounds (represented by numeral 3' in FIG. 5) in the appropriate nerves of the person to increase the quality of "sounds" heard by him.

The mechanism by which the surgically implanted magnetic enhancement pills operate is thought to be the same as the mechanism for the basic transducer 1 (FIG. 1) itself. That is, spacing maintained between an electromagnet and a flux concentrator causes a directional electrical field to be produced that extends beyond the magnetic field, and in the case of the transplanted magnetic pills, the "boosted" directional electric field extends into the adjacent nerves. This was tested upon myself, a hearing person, by placing the "pill" against various areas of the head, ear, upper cortex, etc. and holding the transducer two inches away. The sound was as loud as if the transducer were there in place of the pill so it is believed that the above described boosting or enhancement does occur.

Another proposed application of the Bennewitz transducers of FIGS. 1 and 3C is shown in FIG. 4. The transducer 1 shown in FIG. 1 and the transducer 1' shown in FIG. 3C are used in cooperation with each other to cause an electric signal represented by arrows 51 in FIG. 4 in the right-hand portion of a severed nerve 45A to be sensed, amplified, and injected or induced in the right-hand portion 45B of the severed nerve. The Hall effect device 17 in the transducer 1' senses variations in the magnetic flux contained in rear lobe 13B as a result of variations in the directional E field (designated by reference numeral 47 in FIG. 4) by the moving charges 51 in the left-hand portion of severed nerve 45A.

In accordance with an important aspect of my invention, my experiments have led to the discovery that variations externally introduced in the electric field in the region into which the directional E vector 15 extends cause corresponding variations in the magnetic field associated with the transducers shown in FIGS. 1 and 3C. For this reason, the transducer 1' shown in FIG. 3C incorporates Hall effect transducer 17 in order to sense such variation in the magnetic field and generate an electric signal on the conductors 19C connected to the output of Hall effect sensor 19. (It should be noted that coil 8 in the device of FIG. 1 can also detect variations in the magnetic field caused as a result of externally caused variations in the electric field in a region into which E vector 15B extends. However, the Hall effect device 17 is more efficient for the devices constructed up to now.)

Thus, it can be seen that if the transducer 1' of FIG. 3C is placed against the skin 41 of a person so that the directional magnetic field region 35 and the directional E field region 47 extend into the right-hand portion of severed nerve 45A, transducer 1' produces a signal representative of the nerve signal 51 on the conductors in insulating shield 19D.

Reference numeral 37A in FIG. 4 represents a surgically implanted magnetic pill having an inherent magnetic field indicated by reference numerals 39A and 39B. The interaction of that magnetic field with the beta field 35 enhances the intensity of the E field that passes into the interior of nerve section 45A.

The detected neural signals are amplified by means of amplifier 69, which can be any suitable differential amplifier with its gain adjusted to produce the desired current to be applied to the input leads 3 of coil 9 of transducer 1 shown in FIG. 4. These signals cause the magnetic field associated with transducer 1 (shown in detail in FIG. 1) to be modulated in accordance with the amplified neural signals outputted by amplifier 69. This causes the corresponding variation in the magnetic field region 16 and in intensity of the electric field represented by vector 15B in FIG. 4 and causes movement of ionic charge signals represented by arrows 59, thereby re-creating the nerve signal represented by arrows 51 in the right-hand portion 45 of the severed nerve.

Magnetic pill 37B enhances the E field in the manner previously described. Thus, it is believed that the transducers 1 and 1' described herein can be used to bridge the gaps between severed nerves in the manner shown in FIG. 4 without the necessity of surgically implanting bulky devices through the skin of a person with severed nerves and without the necessity of utilizing invasive procedures requiring cutting of the nerve surface.

Figure 6:
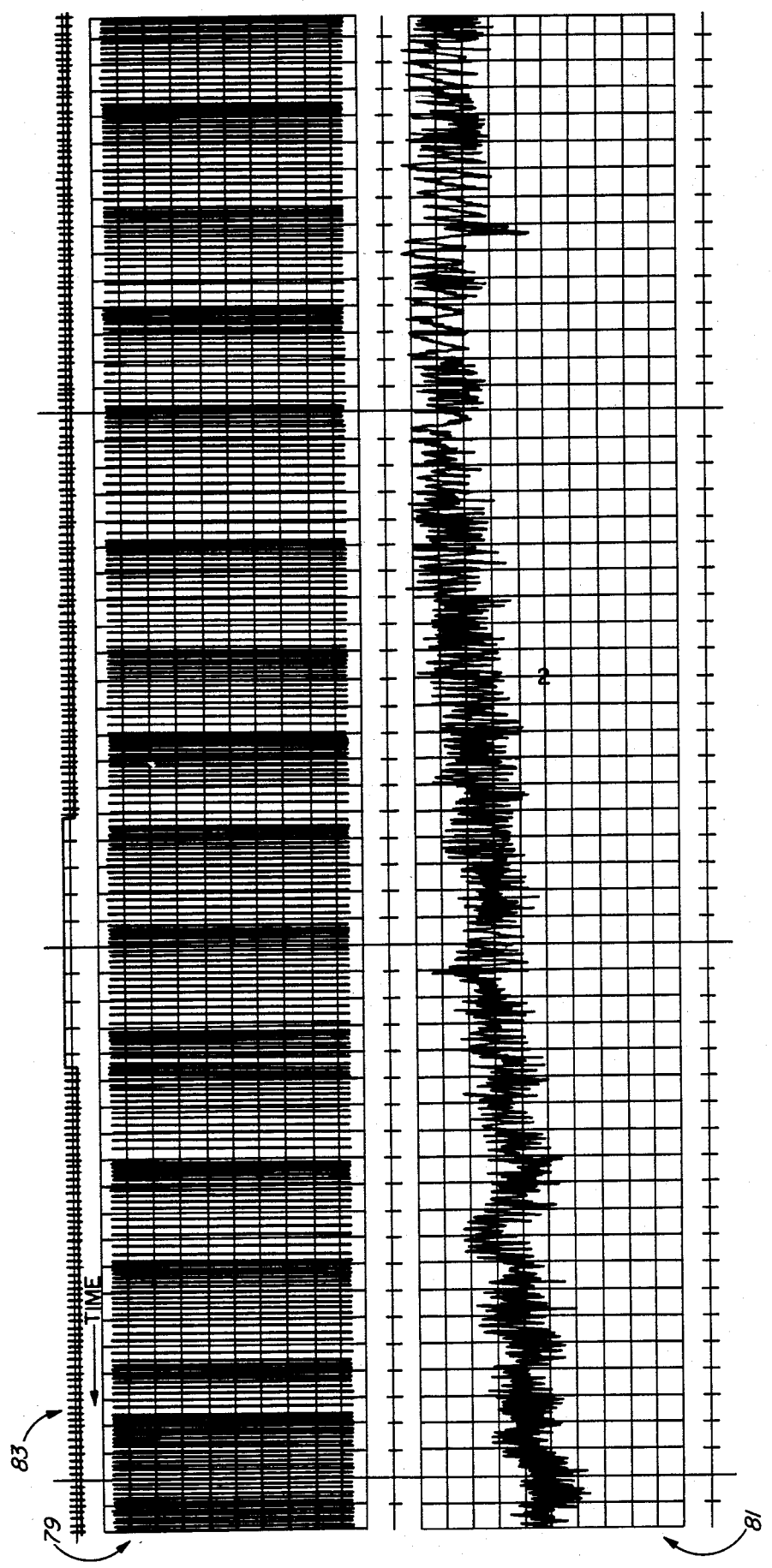
FIG. 6 illustrates waveforms applied to a transmitting device of the present invention to a totally deaf girl and signals obtained by amplifying neural electrical signals detected in her inner ear by means of the sensing device of the present invention.

FIG. 6 discloses a real time plot of output signals produced by a suitable audio amplifier. These signals were applied between input leads such as leads 3 of coil 8 of the transmitter device shown in FIG. 1. This device was positioned beneath the right ear lobe of a seventeen year old girl who is totally deaf. The leading end of the flux concentrator 5 was placed against the skin adjacent to her right ear lobe and oriented so that the electric field vector 15B passed into her inner ear region (as shown in FIG. 5).

The waveform designated by reference numeral 83 in FIG. 6 indicates the time scale. As can be seen from waveform 79, the frequency of the audio signals applied to leads 3 of the transmitting device were repetitively swept over a range of frequencies, leading to the repetitively varying density of the waveform shown in FIG. 6. The range of frequencies represented by waveform 79 varies from approximately 500 cycles per second to approximately 5,000 kilocycles per second. The lower waveform 81 of FIG. 6 represents the amplified output of a receiving device, such as the one shown in FIG. 3C, utilized to detect internal neural responses to the input waveform 79 in the subject seventeen year old girl.

The above-mentioned receiving device 1' of FIG. 3C was positioned behind her left ear, so that the axis of its flux concentrator 29 was aimed into the hearing center of her brain. The girl indicated that she could hear the sounds represented by waveforms 79, which were plotted on a recorder. The amplified output of the receiving device was simultaneously plotted to produce waveform 81.

The increased density (i.e., higher frequency portions) of the detected waveform 81 can be readily seen to correspond to the increased density or higher frequency portions of input waveform 79 in FIG. 6, although there is a slight delay between the high density portions of waveform 81 and the corresponding high density portions of waveform 79.

What is demonstrated by comparison of waveforms 79 and 81 in FIG. 6 is that the transmitter transducer (such as the one shown in FIG. 1 of the present invention) is capable of producing variations in its electric field vector 15B, that the electric field vector 15B extends into the above mentioned portions of the inner ear and produces or induces neural signals therein, and that the sensing device of the present invention (as shown in FIG. 3C) is capable of sensing neural signals because its electric field vector 15B also extends into a nerve conducting the signals produced by the brain in response to the neural signals induced by the transmitting device. The placement of the transmitting device and receiving device on opposite ears and aiming the electric field vector 15B into the hearing center portion of the deaf girl's brain strongly suggests that the correspondence between the high frequency and low frequency portions of input waveform 79 and output waveform 81 is caused by the above described phenomena and is not due to physical coupling between the input and output devices used. The delay between the dense portions of output waveform 81 and input waveform 79 shows that external coupling between input and output transmitting and sensing devices of the present invention is not present and does not cause the above described correspondence between waveforms 79 and 81.

Figure 7:
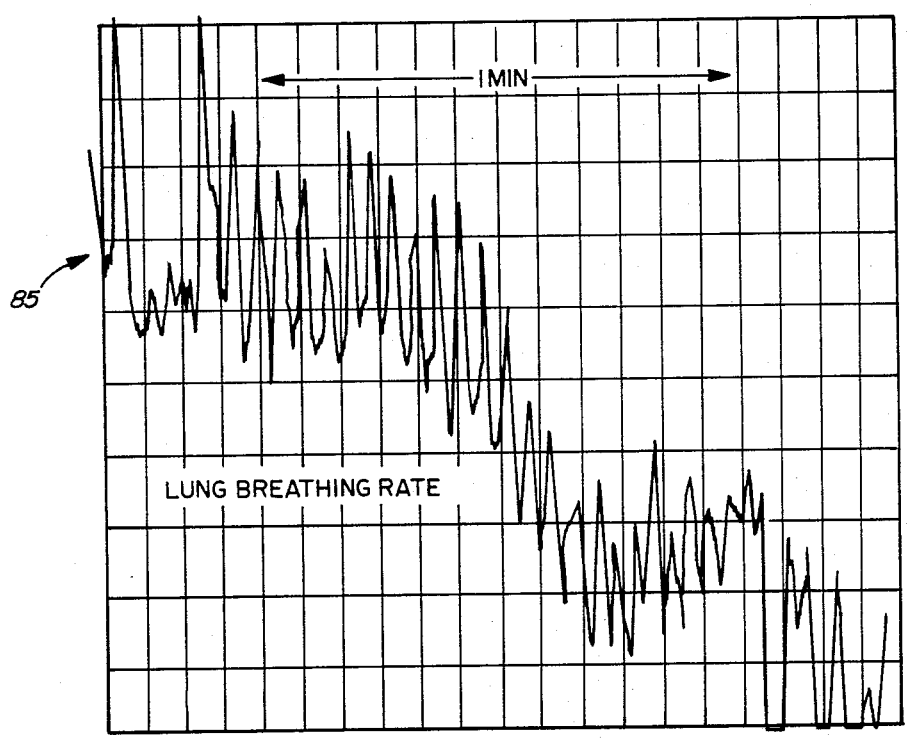
FIG. 7 is a graph showing a waveform produced by placing the sensing device of FIG. 3C against the inventor's chest to cause it to sense neural signals in his lungs associated with his breathing.

FIG. 7 discloses another waveform, designated by reference numeral 85, produced by the output of the sensing device of FIG. 3C further showing that the device is capable of detecting neural signals occurring in the body of a person non-invasively, i.e., without the necessity of causing the sensing device to physically penetrate the skin of the person. More specifically, the graph of FIG. 7 is a substantial copy of a real time plot produced by means of an electronic plotter having its input coupled to a sensing device similar to the sensing device 1' shown in FIG. 3C. The sensing device 1' was positioned so that its flux concentrator 29 was pressed against my skin upwards and to the left of my clavical near the top of my left lung. The axis of its flux concentrator 29 was oriented perpendicularly to my skin at that point. Each cycle of the roughly sinusoidal waveform 85 corresponds to my inhaling and exhaling of one breath and represents sensing of neural signals in my body associated with that inhaling and exhaling. The horizontal distance indicating a time interval of one minute is indicated in FIG. 7.

Figure 9:
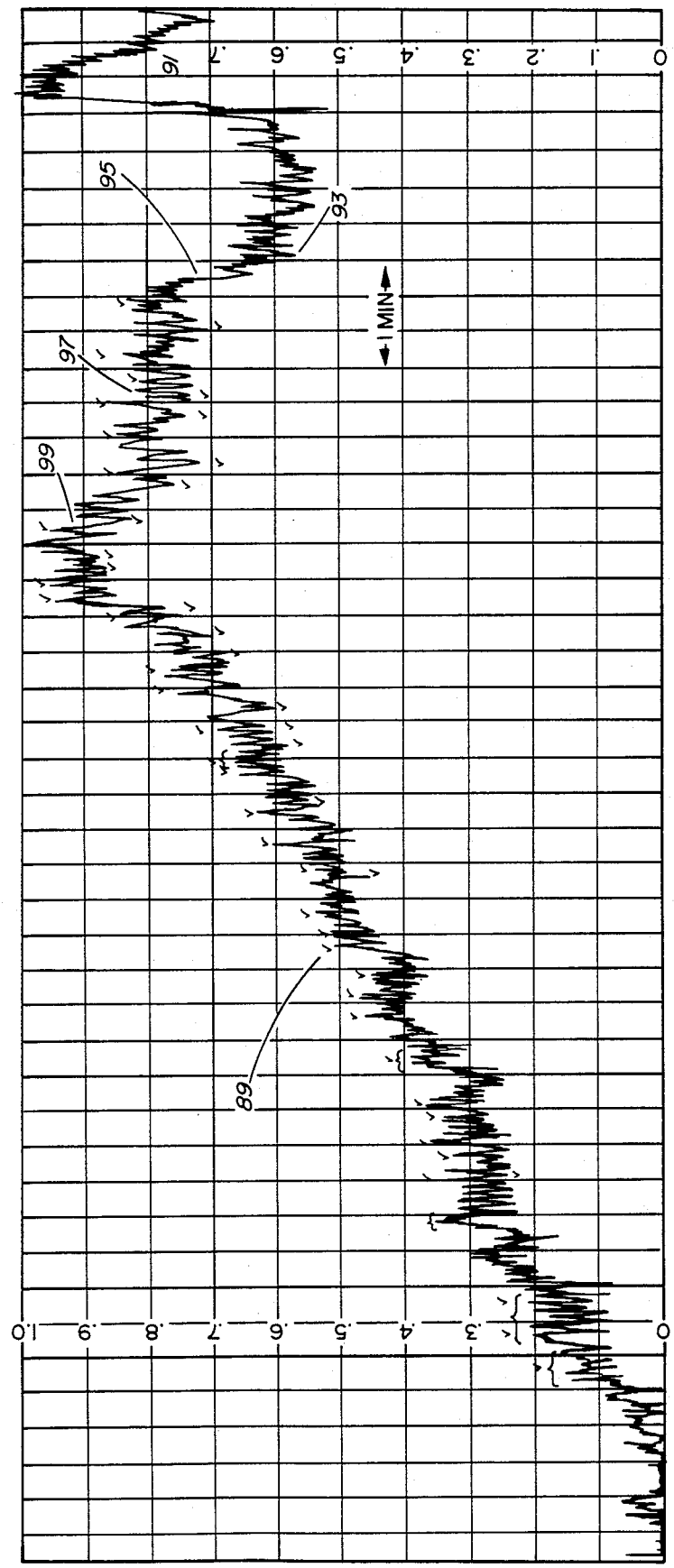
FIG. 9 is a substantial copy of a real time plot, made by an electronic plotter, of the output signal produced by the sensing device of FIG. 3C to sense electrical signals representing blood sugar level in a woman.

Referring now to FIGS. 8A, 8B and 9, it is known that when sugar is ingested by human beings, certain changes are produced in the electrical currents in their blood. In FIG. 9, curve 89 is a substantial copy of a real time plot produced by an electronic plotter in response to output signals produced by a sensing device 1' similar to the one shown in FIG. 3C for my wife. The horizontal axes of the plot shown in FIGS. 8A and 8B and the plot shown in FIG. 9 designates elapsed time, with the direction of the time axes being from right to left. Waveform 87 of FIGS. 8A and 8B designates a similar real time plot taken for myself. In each case, the end of the flux concentrator 29 of the sensing device 1' (FIG. 3C) was placed against the junction of veins in the backs of our respective hands. A small amount of time was allowed for temperature stabilization, which occurred during the period of time indicated by the word "normalizing" on both plots, and designated by reference numeral 91. In FIG. 9, the plotter was adjusted to bring the trace being plotted to the vertical level indicated by the legend "0.6". In the graphs of FIGS. 8A and 8B, the plotter or recorder was "normalized" to bring the level of the trace to the level designated "0.4". For approximately two minutes, nothing was done. Then at the time indicated by 93 in FIG. 9, the subject drank 80 milliliters of tea containing six teaspoons of sugar. As expected, there was a sharp increase, designated by reference numeral 95 in FIG. 9, in the electrical current in the blood flowing through the above mentioned veins on the back of the subject's hand. The signal level then leveled off somewhat, as indicated by reference numeral 97, for approximately several minutes, and then increased to a peak, indicated by reference numeral 99 in FIG. 9. These electrical signal changes represented by reference numerals 95, 97, 99 are a result of a neural response that sends electrical signals to the pancreas to signal the pancreas that sugar is "on the way". This neural reaction is known to be a measure of the sugar content of the blood.

At this point, it should be noted that the blood circulation time in the woman's body is approximately six times per minute. Numerous small "checks" have been made on the graphs of FIGS. 8A, 8B and 9 indicating positive and negative peaks. These peaks indicate when the portion of the blood passing through the vein adjacent to the sensing device 1' has a high sugar concentration. (The electrical activity in the blood is a function of insulin level therein. The presence of sugar, oxygen, iron and other constituents of the blood also affect the electrical activity.)

The sugar acts as a "tracer" as the blood is circulated approximately six times per minute. Where the check marks near waveforms 87 and 89 begin to disappear, this indicates that the peaks that are spaced 1/6 of a minute apart are beginning to disappear, indicating that the sugar has been absorbed into the blood as a result of the body's reaction by injecting corresponding amounts of insulin into the blood.

Referring to FIG. 8B, which is the extended portion of waveform 87, reference numerals 101 and 103 and 105 indicate electrical activity as insulin is released into the blood in response to the sugar intake which occurred at the point designated by reference numeral 107 in FIG. 8A. The pulse 101 was detected as a result of blood containing insulin therein flowing past the sensing device held against my above-mentioned vein junction. Reference numerals 103 and 105 indicate detection of the result of additional quantities of insulin released into my blood.

The main point of the information shown by waveform 87 of FIGS. 8A and 8B and waveform 89 of FIG. 9 is that these waveforms show that the sensing device 1' of FIG. 3C functions to indicate electrical activity in the blood as a result of ingestion of sugar. This is done with no penetration of the skin by any physical device. This indicates that the electrical field in the blood flowing through the above-mentioned vein junctions causes variation in the electrical field in the region 15A, and that this produces corresponding variations in the magnetic sphere 13A' and 13B' of FIG. 3C. This, in turn, produces corresponding variations in output of the Hall effect device 17. The results correspond to what would be expected for a normal human male and a normal human female. Thus, it appears that the sensing device of FIG. 3A could be utilized to inexpensively produce a non-invasive sugar level sensing device that could activate an alarm for diabetic persons, indicating when it is necessary for them to receive insulin injections.

Note also that a sugar level test producing information comparable to that shown in FIG. 9 takes approximately five hours if conventional techniques are used.

This is believed to be the first time anyone has ever managed to monitor electrical signals occurring inside the body, and inside the blood without performing any type of physical penetration of the skin of a person.

Figure 10:
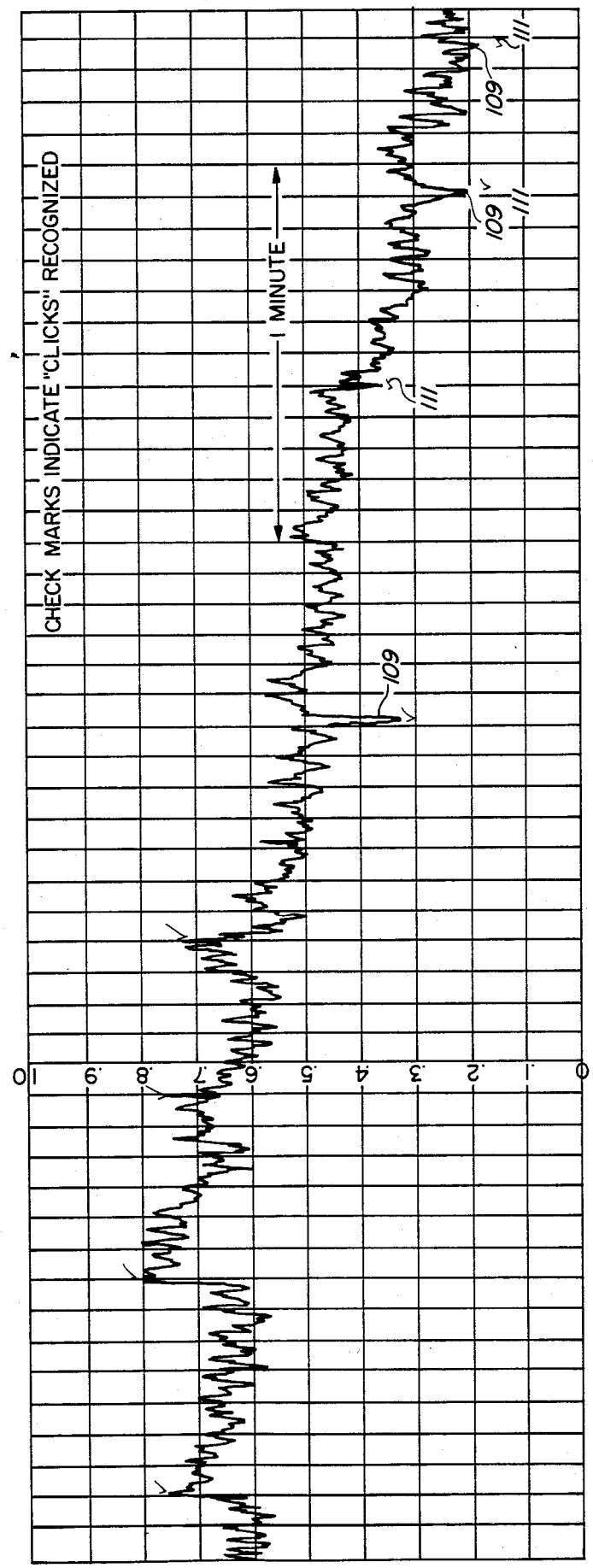
FIG. 10 is a substantial copy of a real time plot made of amplified signals, generated in the hearing center of my brain in response to audible clicks, and detected by the sensing device of FIG. 3C.

FIG. 10 is a substantial copy of a real time plot of signals sensed by the device of FIG. 3, amplified by an amplifier and fed to the input of an electronic plotter when the sensing device 1' of FIG. 3 is positioned above my right ear so that the axis of flux concentrator 29 is aimed at the hearing center of my brain. The hearing center of a human brain is connected to the inner ear by a nerve trunk and responds to neural signals received from the inner ear in response to sounds impinging on the ear drum. In the experiment in which the plot of FIG. 10 was made, the plotting paper moved at the rate of approximately three inches per minute. At the times indicated by check marks such as 111 in FIG. 10, a clicking sound was made in my left ear. The clicking sound was made by another person, and was accomplished by "clicking" together the fingernail of the index finger and her thumb nail. This produced a clicking sound which was clearly audible in my left ear, but could not be heard by my right ear.

As is apparent from the real time plot of FIG. 10, an immediate response to each of the clicks can be seen in the illustrated waveform. Reference numeral 109 designates some of the deviations in the waveform corresponding to various ones of the clicks. This correspondence is believed to demonstrate that the sensing device of FIG. 3 non-invasively detects neural signal activity produced by the human brain in response to audatory stimulus.

While the invention has been described with reference to several particular embodiments thereof, those skilled in the art will be able to make various modifications to the disclosed apparatus and method without departing from the true spirit and scope of the invention.

I claim:
1. A method for producing an extending, highly directional electrical field, said method comprising the steps of:
    (a) placing a plurality of magnets end to end so that opposite poles of the respective adjacent magnets are adjacent; and
    (b) positioning a paramagnetic flux concentrating element having first and second ends and a longitudinal axis so that the longitudinal axis is approximately aligned with the axes of said plurality of magnets and said first end of the flux concentrating element is located a predetermined distance from the closest magnet, said positioning of said flux concentrating element causing a directional electric field to extend outwardly from said second end of the flux concentrating element and beyond a magnetic field produced by said magnets and said flux concentrating element, the directional electric field decreasing approximately linearly along a line colinear with the axis of said flux concentrating element.

2. The method of claim 1 including the steps of varying the electric field in the region in which said directional electric field extends to produce a corresponding variation in said magnetic field, using a magnetic sensing device to detect said corresponding variation and to produce a sense signal in response to said corresponding variation, and amplifying said sense signal.

3. The method of claim 1 including the step of varying said magnetic field to produce a corresponding variation in said directional, outwardly extending electric field.

4. The method of claim 3 including the step of aiming said directional, outwardly extending electric field into a region containing electrically charged particles to cause variations in the movement of said electrically charged particles corresponding to said varying of said magnetic field.

5. The method of claim 2 including the step of aiming said directional, outwardly extending electric field into a nerve, said varying of said electric field being caused by movement of charged ions in said nerve which causes electrical currents to flow in said nerve, variations in said amplified sense signal representing variations in said electrical current in said nerve.

6. The method of claim 4 wherein said region is within a nerve, said variation in movement of electrically charged particles causing a variation in current in said nerve corresponding to said varying of said magnetic field.

7. The method of claim 2 including the step of positioning said magnets and said flux concentrating element so that said directional electric field extends into a vein carrying blood, said varying of the electric field, in the vein in which said directional electric field extends, being caused by electrical activity in the blood representative of sugar level in the blood.

8. The method of claim 4 wherein said region containing electrically charged particles is in a nerve, said variations in said directional, outwardly extending electric field causing corresponding variation in the electrical current in said nerve.

9. The method of claims 5 or 8 wherein said nerve is located in a human or animal brain.

10. A method for producing an extending, highly directional electrical field, said method comprising the steps of:
(a) placing a magnet in a predetermined position; and
(b) positioning a paramagnetic flux concentrating element having a longitudinal axis so that the longitudinal axis is roughly parallel with the axis of said magnet and the end of said concentrating element is located a predetermined distance from said magnet, said positioning of said flux concentrating element causing a directional electric field to extend outwardly from a second end of the flux concentrating element, beyond a magnetic field produced by said magnet and said flux concentrating element, the directional electric field decreasing along a line colinear with the axis of said concentrating element.

11. A device for producing an outwardly extending, directional electric field, said device comprising:
(a) magnetic means having a north pole and a south pole;
(b) paramagnetic flux concentrating means for concentrating magnetic flux flowing through said magnetic means, said flux concentrating means having a first end and a second end; and
(c) spacing means for maintaining said first end of said flux concentrating means in predetermined spaced relationship to said magnetic means to cause said device to produce a directional electric field extending outwardly from said second end of said flux concentrating means along an axis of said flux concentrating means, the electric field strength of said directional electric field decreasing along said axis with increasing distance from said second end.

12. The device of claim 11 wherein said magnetic means includes a plurality of magnets disposed adjacent to each other, one type of magnetic pole of each of said plurality of magnets facing an opposite type magnetic pole of another of said magnets.

13. The device of claim 12 wherein said magnets are permanent magnetic discs.

14. The device of claim 11 wherein said spacing means includes a diamagnetic material disposed between said magnetic means and said flux concentrating means.

15. The device of claim 11 wherein said north pole of said magnetic means faces away from said flux concentrating means.

16. The device of claim 11 wherein said south pole of said magnetic means faces away from said flux concentrating means.

17. The device of claim 11 including first means for varying the flux in said flux concentrating means in response to an external signal to cause corresponding variations in said directional electric field.

18. The device of claim 17 wherein said first means includes a coil disposed around said flux concentrating means, said coil having a pair of terminals across which said signal is applied.

19. The device of claim 11 including sensing means for sensing variations in the magnetic flux produced by said device.

20. The device of claim 19 wherein said sensing means includes a coil.

21. The device of claim 19 wherein said sensing means includes a Hall effect sensor disposed adjacent to said magnetic means.

22. The device of claim 12 wherein one of said magnets is separated from another of said magnets by means of an indium wire coil to compensate for temperature variation in the magnetic field produced by said device.

23. The device of claim 17 in a hearing aid device wherein said signal represents audio sounds, said device being encapsulated in a housing and oriented to aim said directional electric field region into the inner ear of a person to aid the person's hearing.

24. The device of claim 17 in a medical probing device wherein said directional electric field region is aimed into a nerve to produce a nerve signal in response to said external signal without physical invasion or severing of said nerve.

25. The device of claim 19 in a medical probing device wherein said directional electric field is aimed into a nerve to cause said device to produce variations in the magnetic field produced by said device in response to variations in an electrical nerve signal in said nerve, said sensing means producing an output signal that varies in correspondence with said variations in said electrical nerve signal.

* * * * *